United States Patent [19]

Draguez Tripels de Hault et al.

[11] 4,087,379

[45] May 2, 1978

[54] CATALYST AND PROCESS FOR OLIGOMERIZING OLEFINS

[75] Inventors: Emmanuel R.E.G. Draguez Tripels de Hault, Waterloo; Marcel Van Tongelen, Diegem; Henri R. Debus, Meise, all of Belgium

[73] Assignee: Labofina S. A., Brussels, Belgium

[21] Appl. No.: 445,876

[22] Filed: Feb. 26, 1974

[30] Foreign Application Priority Data

Mar. 8, 1973 Belgium ................................. 12850

[51] Int. Cl.$^2$ ........................ B01J 31/24; B01J 31/22
[52] U.S. Cl. ............................. 252/429 B; 252/431 R; 260/683.15 D
[58] Field of Search ...................... 252/429 B, 431 R

[56] References Cited

U.S. PATENT DOCUMENTS

| | | | |
|---|---|---|---|
| 2,969,408 | 1/1961 | Nowlin et al. | 252/431 R X |
| 3,413,376 | 11/1968 | Cleary | 252/429 B X |
| 3,485,881 | 12/1969 | Zuech | 252/429 B X |
| 3,485,892 | 12/1969 | Griffin et al. | 252/429 B X |
| 3,511,891 | 5/1970 | Taylor et al. | 252/429 B X |
| 3,577,395 | 5/1971 | Lal et al. | 252/429 B X |
| 3,717,613 | 2/1973 | Ichikawa et al. | 252/431 R X |
| 3,808,283 | 4/1974 | Schneider | 260/666 A |
| 3,876,721 | 4/1975 | Yasui et al. | 252/429 B X |

OTHER PUBLICATIONS

Considine, Chemical & Process Technology Encyclopedia, (1974), Pub. by McGraw-Hill, Inc., p. 904.

*Primary Examiner*—Patrick P. Garvin

[57] ABSTRACT

A catalytic system for oligomerizing olefins comprising (1), an aluminum compound of formula $Al(R)_nX_{3-n}$ or a mixture of such compounds, wherein R is a straight chain or branched alkyl radical containing from 2 to 18 carbon atoms, $n$ is 1, 2 or 3 and X is a halogen, (2), an organic complex of a metal of Group VIII of the periodic table, and (3), a promotor comprising a compound of formula R'X wherein R' is a straight chain or branched alkyl radical containing from 3 to 12 carbon atoms, substituted or unsubstituted, and X is a halogen, the molar ratio of promotor to aluminum compound being between 0.05 and 20.

13 Claims, No Drawings

CATALYST AND PROCESS FOR OLIGOMERIZING OLEFINS

The present invention relates to the use of a new catalytic system for the oligomerization of olefins of low molecular weight. More particularly, the present invention relates to the dimerization and/or codimerization of olefins, especially propylene.

It is known that olefinic hydrocarbons may be transformed into olefins of higher molecular weight, by using an alkylaluminium together with nickel or a nickel salt. In such process, the aluminium compound and nickel or nickel compounds promote selectively in transforming olefins into oligomers. Since, certain operative difficulties result from the use of colloidal nickel, organic complexes of nickel are preferably used. Catalytic systems comprising an organometallic aluminium halide and an organic nickel complex are homogeneous and oligomers of olefins are prepared with these systems under mild reaction conditions (U.S. Pat. No. 2,969,408 and French Pat. No. 1,519,181).

An object of the present invention is to provide a new and improved and new catalytic system.

Another object of this invention is to provide a new and improved catalyst system and process for oligomerizing olefins.

The present invention which fulfills these and other objects, is in one of its embodiments, a catalyst system for the oligomerization of olefins which comprises (1) an $Al(R)_n X_{3-n}$ type compound or a mixture of such compounds, wherein R is a straight chain or branched alkyl radical containing from 2 to 18 carbon atoms, n is 1, 2 or 3, and X is a halogen;

(2) an organic complex of a metal of Group VIII of the periodic table, and (3) a promotor consisting of an R'X type compound, wherein R' is a straight chain or branched alkyl radical containing from 3 to 12 carbon atoms, which may be substituted or unsubstituted and X is a halogen, the molar ratio of promotor to aluminium compound being comprised between 0.05 and 20. If substituted, R' will be substituted with an aryl or cycloalkyl radical.

In another embodiment the present invention is a process for oligomerizing olefins, in the presence of the above described catalytic system, at a temperature of from $-40°$ to $+120°$ C, under pressure conditions such that the reactants are preferably maintained in liquid or condensed phase.

According to a preferred embodiment of the invention, the catalytic system contains an organo-aluminium compound having the general formula $AlR_2X$ or $AlRX_2$, or a mixture of such compounds, wherein R and X are as above defined. Particularly preferred is an organo-aluminium compound or a mixture of compounds of the preferred formula wherein R is an ethyl, propyl or butyl radical. No advantage is obtained from the use of an organo-aluminium compound in which R contains more than 18 carbon atoms. In the compound having the formula $AlR_2X$, both R radicals may be the same or different. Diethylaluminium monochloride, ethylaluminium dichloride and their mixtures are easily available and are therefore preferably used.

The catalytic system comprises, beside the above described aluminium compound, an organic complex of metal of Group VIII of the periodic table, such as cobalt or preferably nickel. This complex generally includes Lewis bases such as phosphine, arsine or a chelating group. For instance, the organic complex may be nickel acetylacetonate, nickel benzoylacetonate, and compounds having the general formula $Ni[P(R'')_3]_2X_2$ wherein X is a halogen and R'' is an alkyl, cycloalkyl or aryl radical. A phosphine wherein the R'' radical is a radical of low molecular weight is preferably used, the activity of the catalytic system by weight unity being high. Dichlorobis (trialkylphosphine) nickel wherein the alkyl radical is the methyl, ethyl, n- or iso-propyl, n- or isobutyl radical, or dichlorobis (triphenylphosphine) nickel or dichlorobis (tricyclohexylphosphine) nickel are preferred.

In the catalytic system of the present invention, the aluminium compound is used in an amount, expressed in a molar ratio to the nickel compound, greater than 1. Preferably, this molar ratio is between 2 and 100.

Hydrochloric acid and nitric acid have been suggested as promotors for such catalytic systems. However, the problems of corrosion which occur by using such promotors, render their use uneconomic in industrial scale operations. Other promotors such as water have also been suggested to increase the conversion rate of the starting olefin. However, the use of water presents drawbacks, such as formation of solid deposits in the reactor. According to the present invention, an alkyl halide containing from 3 to 12 carbon atoms is added to the catalytic system, more particularly a chloride and especially a tert-alkyl chloride, such as tert-amyle chloride, 2-chloro-2-methylhexane, tert-butyl chloride. Such compounds confer to the catalytic system a greatly increased activity. This result is unexpected since tert-butyl chloride has been reported as being a poison for polymerization catalysts of the Friedel-Crafts type.

The amount of promotor, expressed in a molar ratio to the organo-aluminium compound, does not exceed 20 and may be as low as 0.05. Preferably, the promotor is used in a molar ratio to the organo-aluminium compound of between 0.1 and 6.

Generally, the dimerization reaction of the present invention is performed at a temperature varying between about $-40°$ and $+120°$ C, preferably between $0°$ and $100°$ C. The reaction generally is carried out at a pressure varying between 1 and 60 atmospheres, although lower pressures than atmospheric pressure or pressures higher than 60 atmospheres may be used. Generally, temperature and pressure are controlled to maintain the reaction medium in the liquid phase. The choice of the temperature depends on the particular olefin used and on the degree of oligomerization desired. A temperature between 0 and $80°$ C is more favorable than a higher temperature for the dimerization of propylene.

The reaction may be performed in the presence of an inert organic solvent such as paraffin, a cycloparaffin, an aromatic hydrocarbon or a halogenated hydrocarbon, particularly an aromatic halogenated hydrocarbon such as chlorobenzene.

The characteristics of the present invention are illustrated by, but not limited to the following examples:

EXAMPLE 1

Dichloro-bis(tributylphosphine) nickel (50 mg) under a nitrogen stream was introduced into a reactor followed by introduction of 100 cm$^3$ of propylene into the reactor. The mixture was stirred with a magnetic stirrer and the autoclave was maintained at a temperature of $30°$ C and under a pressure of from 11 to 13 Kg/cm$^2$.

Diethylaluminium monochloride (0.5 g) was then introduced by injection under pressure, said chloride being swept in by 50 cm³ of propylene. The instant of this injection was considered as being the initial time of the reaction (time zero). 30 minutes after the initial time, an an additional 150 cm³ of propylene was introduced. 4 successive additions of promotors were then performed at, respectively, 40, 50, 60 and 70 minutes after the initial time. The amount of promotor was such that the cumulative molar ratios of promotor to aluminium compound after each addition were, respectively 1, 3, 8 and 18. During each such addition, the promotor was swept into the reaction mixture with 40 cm³ of propylene. After 80 minutes of reaction time, a last introduction of propylene was performed, so that the total amount of propylene used was 500 cm³. After 90 minutes of reaction time, the propylene, which did not react, was evacuated, and the reaction product was withdrawn and washed with an alkaline solution 0.1N, and then with water.

By using the above procedure, several experiments were performed in the presence of various promotors. The results of the experiments are shown in the following table and for comparison, the results of a similar experiment without any promotor.

| Promotor | Conversion of $C_3H_6$ (% by weight) based on the used $C_3H_6$ |
|---|---|
| 1-chlorobutyl | 35.3 |
| 2-chlorobutyl | 56.1 |
| tert-butyl chloride | 73.9 |
| tert-butyl bromide | 51.3 |
| tert-amyle chloride | 66.7 |
| 2-chloro-2-methylhexane | 65.6 |
| water | 67.3 |
| no promotor | 15.6 |

EXAMPLE 2

The procedure of Example 1 was repeated, but with the use of 21.5 mg of nickel acetylacetonate was used instead of the dichloro-bis(tributylphosphine). The promotor employed was tert-butyl chloride. The conversion rate of propylene was 44.1%.

EXAMPLE 3

The procedure of Example 1 was again repeated except that the propylene was treated at a temperature of 40° C and under a pressure of 40 Kg/cm² in the presence of a catalytic system containing ethylaluminium dichloride, bis(tricyclohexylphosphine) Ni dichloride and tert-butyl chloride (molar ration = 5 to the aluminium compound). The conversion rate of propylene was 63.5%.

EXAMPLE 4

The procedure of Example 1 was again repeated, but with the use of tert-butyl chloride as promotor, in the presence of diethylcyclohexane as solvent. The conversion rate of propylene was 68.6%. Similar results were obtained by using diethylbenzene, toluene, iso-octane, cyclohexane and chlorobenzene as the solvent.

EXAMPLE 5

The procedure of Example 1 was again repeated with the exception that ethylene was used as the olefin and the reaction was performed at 20° C and under a pressure of 30 Kg/cm², in the presence of diethylbenzene as solvent. The aluminium compound was introduced into the reactor with the solvent. The promotor employed was tert-butyl-chloride. The product obtained largely consisted of butenes, particularly 2-butene.

A similar experiment, performed at 75° C, gave a mixture containing a larger proportion of olefins containing 6 carbon atoms and more.

EXAMPLE 6

The procedure of Example 1 was again repeated, but by using a mixture containing equal volumes of ethylene and propylene. This mixture was treated at a temperature of 0° C and under a pressure of 20 Kg/cm², in the presence of a catalytic system consisting of equal volumes of diethylaluminium monochloride and ethylaluminium dichloride, together with bis(trihexylphosphine) nickel dibromide and tert-butyl chloride, the molar ratio of the promotor to the aluminium compound being 5. n-hexane was added as solvent. The product obtained consisted mostly of $C_6$ olefins and $C_5$ olefins, these latter mainly consisting of pentenes and 2-methyl-butene.

EXAMPLE 7

The procedure of Example 1 was repeated in three experiments, but in the presence of a catalytic system containing ethylaluminium dibromide, bis(triisopropylphosphine) nickel dibromide and dodecyl bromide, in the presence of chlorobenzene as solvent. The three experiments were performed by varying the molar ratio aluminium compound/nickel compound. In each experiment, the molar ratio of promotor to aluminium compound was maintained equal to 3. The following results were obtained:

| Molar ratio Aluminium compound/nickel compound | Conversion of $C_3H_6$ (% to used $C_3H_6$) |
|---|---|
| 20 | 56.7 |
| 40 | 63.1 |
| 85 | 63.8 |

EXAMPLE 8

An experiment for dimerizing propylene was performed in a continuous phase, under a pressure of 25 Kg/cm² and at an average temperature in the reactor of 61.8° C. The catalytic system used consisted of a mixture of diethylaluminium monochloride and ethylaluminium dichloride, dichloro bis (tributylphosphine) nickel and tert-butyl chloride with a ponderal ratio Al/Ni = 19.9. The amount of nickel complex was 60.2 g and that of tert-butyl chloride was 227, both amounts being expressed in parts by weight to one million parts by weight of propylene used. The residence time in the reactor (calculated from the formula (60 × reactor volume in cm³) (volume of introduced $C_3H_6$ in cm³) was 19.3 minutes. The conversion rate into oligomers of the propylene was 93.4% with a selectivity to dimers of 82.4%.

The conversion rate and/or selectivity may vary by modifying certain operative conditions, more particularly reaction temperature and the promotor agent concentration.

What is claimed is:

1. A catalytic system for dimerizing and codimerizing olefins, consisting essentially of:
   a. an aluminum compound of the formula $Al(R)_nX_{3-n}$ or a mixture of such compounds, wherein R is a straight chain or branched alkyl radical containing from 2 to 18 carbon atoms, n is 1,2, or 3, and X is a halogen;

b. an organic complex of a metal of Group VIII of the periodic table with an organic moiety selected from the group consisting of acetylacetonate, benzoylacetonate, and complexes of the formula $(P(R'')_3)_2X_2$ wherein X is halogen, and R'' is an alkyl, cycloalkyl, or aryl radical; and c. a relative amount of sufficient to promote catalytic formation of dimers and codimers of a promotor comprising a compound of formula R'X wherein R' is a straight chain or branched chain alkyl radical containing from 3 to 12 carbon atoms, which may be optionally substituted with an aryl or cycloalkyl group, and X is a halogen.

2. The catalytic system of claim 1, wherein the promotor is used in an amount, expressed in molar ratio to the aluminum compound, of between about 0.05 and 20.

3. The catalytic system of claim 2, wherein the molar ratio between the promotor and the aluminum compound is between about 0.1 and 6.

4. The catalytic system of claim 1, wherein the molar ratio between the aluminum compound and the Group VIII metal organic complex is greater than 1.

5. The catalytic system of claim 4, wherein the molar ratio between the aluminum compound and the Group VIII metal organic complex is between about 2 and 100.

6. The catalytic system of claim 1, wherein the Group VIII metal organic complex is a nickel organic complex.

7. The catalytic system of claim 6, wherein the nickel organic complex is a compound of the formula Ni$[P(R'')_3]_2X_2$ wherein X is a halogen and R'' is an alkyl, cycloalkyl, or aryl radical.

8. The catalytic system recited in claim 7, wherein R'' is selected from the group consisting of methyl, ethyl, propyl, isopropyl, butyl, isobutyl, cyclohexyl, and phenyl radicals.

9. The catalytic system of claim 8, wherein said nickel organic complex is Dichloro-bis(tributylphosphine) nickel.

10. The catalyst system of claim 1, wherein said aluminum compound is selected from the group consisting of diethylaluminum monochloride, ethylaluminum dichloride, and mixtures thereof.

11. The catalytic system recited in claim 1, wherein the X group of said promotor is chlorine.

12. The catalytic system recited in claim 11, wherein the R' group of said promotor is a tertiaryalkyl group.

13. The catalytic system of claim 12, wherein said promotor is tert-butylchloride.

* * * * *